US005663316A

United States Patent [19]
Xudong

[11] Patent Number: 5,663,316
[45] Date of Patent: Sep. 2, 1997

[54] BBC6 GENE FOR REGULATION OF CELL DEATH

[75] Inventor: Yin Xudong, Mountain View, Calif.

[73] Assignee: Clontech Laboratories, Inc., Palo Alto, Calif.

[21] Appl. No.: 665,617

[22] Filed: Jun. 18, 1996

[51] Int. Cl.$^6$ ................................................. C07H 21/04
[52] U.S. Cl. ......................................... 536/23.5; 536/23.1
[58] Field of Search .................................. 536/23.1, 23.5

[56] References Cited

PUBLICATIONS

Garcia, I. et al. (1992) "Prevention of Programmed Cell Death of Sympathetic Neurons by the *bcl*–2 Proto–Oncogene" Science 258:302–304.

Hengartner, M.O., H.R. Horvitz (1994) "C. elegans Cell Survival Gene ced–9 Encodes a Functional Homolog of the Mammalian Proto–Oncogene bcl–2" Cell 76:665–676.

Kozopas, K.M. et al. (1993) "*MCL1*, a gene expressed in programmed myeloid cell differentiation, has sequence similarity to BCL2" Proc. Natl. Acad. Sci. USA 90:3516–3520.

Lin, E.Y. et al. (1993) "Characterization of A1, a Novel Hemopoietic–Specific Early–Response Gene with Sequence Similarity to bcl–2" The Journal of Immunology 151(4):1979–1988.

Oltavai, Z.N. et al. (1993) "Bcl–2 Heterodimerizes In Vivo with a Conserved Homolog, Bax, That Accelerates Programmed Cell Death" Cell 74:609–619.

Strasser, A. et al. (1991) "bcl–2 Transgene Inhibits T Cell Death and Perturbs Thymic Self–Censorship" Cell 67:889–899.

Vaux, D.L. et al. (1988) "Bcl–2 gene promotes haemopoietic cell survival and cooperates with c–mycl to immortalize pre–B cells" Nature 335:440–442.

Williams, G.T., C.A. Smith (1993) "Molecular Regulation of Apoptosis: Genetic Controls on Cell Death" Cell 74:777–779.

Yin, X.–M. et al. (1994) "BH1 and BH2 domains of Bcl–2 are required for inhibition of apoptosis and heterodimerization with Bax" Nature 369:321–323.

Yang, E. et al. (1995) "Bad, a Heterodimeric Partner for Bcl–$x_l$ and Bcl–2, Displaces Bax and promotes Cell Death" Cell 80:285–291.

Boise, L.H. et al. (1993) "bcl–x, a bcl–2–related gene that functions as a dominant regulator of apopototic cell death" Cell 74:597–608.

Vaux, D.L. (1992) "Prevention of programmed cell death in *Caenorhabditis elegans* by human bcl–2" Science 258:1955–1957.

*Primary Examiner*—Christina Y. Chan
*Assistant Examiner*—Emma Cech
*Attorney, Agent, or Firm*—Saliwanchik, Lloyd & Saliwanchik

[57] ABSTRACT

The subject invention provides new proteins which are involved in the regulation of cell death. Also provided are nucleotide sequences which encode the novel proteins. Further aspects of the invention include antibodies to the novel proteins, and diagnostic and therapeutic methods.

2 Claims, No Drawings

BBC6 GENE FOR REGULATION OF CELL DEATH

BACKGROUND OF THE INVENTION

Strict regulation of cell cycle progression, including differentiation, senescence, and cell death, is critical for the proper development and maintenance of tissues. Dysfunction of the regulation of these processes can result in devastating pathological conditions including, for example, cancer.

One aspect of a normal cell cycle includes biochemically regulated cell death, also known as apoptosis. Regulators of apoptosis, both positive and negative, have been identified. For example, the protein known as Bcl-2 counters a variety of apoptotic stimuli (Vaux et al., 1988; Strasser et al., 1991; Garcia et al., 1992). CED-9, the homolog of Bcl-2 in the nematode *Caenorhabditis elegans*, is found to repress apoptosis in cells that are normally expected to die during the nematode's development. Studies involving transgenic worms expressing Bcl-2 indicate that Bcl-2 can substitute for CED-9 functionally in preventing at least some cell death in these nematodes. (Vaux et al., 1992; Hengartner and Horvitz, 1994).

Many Bcl-2 related proteins share homology within two conserved regions: Bcl-2 homology domains 1 and 2 (BH1 and BH2) (Williams and Smith, 1993; Yin et al., 1994). These proteins include Bax, Bcl-$x_L$, Mcl-1, and A1 (Olwai et al., 1993; Boise et al., 1993; Kozopas et al., 1993; Lin et al., 1993). Several of these proteins are cell death regulators; for example, Bcl-$x_L$ represses apoptosis, while its short form, Bcl-$x_S$, favors cell death. Additionally, Bax in excess interferes with the ability of Bcl-2 to repress apoptosis. Bax homodimerizes and also heterodimerizes with Bcl-2 (Oltvai et al., 1993). Single amino acid substitutions have been found to disrupt Bcl-2-Bax heterodimers, but not Bcl-2-Bcl-2 homodimers. Bcl-2 mutants that did not complex with Bax could no longer repress apoptosis (Yin et al., 1994). These data suggest that the cell cycle regulatory functions of these proteins occur at least partially through protein-protein interactions.

Bad, the Bcl-$x_L$/Bcl-2-associated death promoter homolog, is conserved within the BH1 and BH2 domains (Yang, E., J. Zha, J. Jockel, L. H. Boise, C. B. Thompson, S. J. Korsmeyer [1995] *Cell* 80:285–291). Bad has been shown to heterodimerize with Bcl-xL and Bcl-2, but not with other related proteins. One way in which Bad promotes mammalian cell death is by displacing Bax from Bcl-$x_L$ as it heterodimerizes with Bcl-$x_L$.

BRIEF SUMMARY OF THE INVENTION

The subject invention concerns polynucleotide sequences which encode proteins that regulate mammalian cell death. Specifically exemplified herein is a gene designated BBC6.

The subject invention concerns novel polynucleotide sequences as well as the proteins encoded by these sequences. A further aspect of the subject invention concerns antibodies which can be raised to the novel proteins of the subject invention.

The polynucleotide sequences, proteins, and antibodies of the subject invention are useful for diagnostic and therapeutic procedures.

BRIEF DESCRIPTION OF THE SEQUENCES

SEQ ID NO. 1 is a nucleotide sequence encoding bbc6.

SEQ ID NO. 2 is the deduced amino acid sequence of the protein encoded by the polynucleotide sequence of SEQ ID NO. 1.

DETAILED DISCLOSURE OF THE INVENTION

The subject invention concerns polynucleotide sequences encoding proteins which regulate mammalian cell death. Specifically exemplified herein is a gene designated BBC6. In a preferred embodiment of the subject invention, the proteins of the subject invention regulate cell death through interactions with Bcl-2.

The unique polynucleotide sequences of the subject invention include sequences which encode the BBC6 proteins, as well as sequences which drive the expression of these proteins.

In one embodiment of the subject invention, the proteins encoded by the genes described herein can be used to raise antibodies which in turn can be used in diagnostic or therapeutic applications.

In one embodiment of the invention, the biological activity of the BBC6 proteins of the subject invention can be reduced or eliminated by administering an effective amount of an antibody to BBC6. Alternatively, the activity of the BBC6 protein can be controlled by modulation of expression of the BBC6 protein. This can be accomplished by, for example, the administration of antisense DNA.

In a further embodiment, the protein of the subject invention can be used as a molecular weight standard. The full-length BBC6 protein shown in SEQ ID NO. 2 has a molecular weight of about 18.4 kDa.

As those of ordinary skill in the art will appreciate, any of a number of different nucleotide sequences can be used, based on the degeneracy of the genetic code, to produce the cell death regulatory proteins described herein. Accordingly, any nucleotide sequence which encodes the cell death regulatory proteins described herein comes within the scope of this invention and the claims appended hereto. Also, as described herein, fragments of the cell death regulatory proteins are an aspect of the subject invention so long as such fragments retain the biological activity so that such fragments are useful in therapeutic and/or diagnostic procedures as described herein. Such fragments can easily and routinely be produced by techniques well known in the art. For example, time-controlled Bal31 exonuclease digestion of the full-length DNA followed by expression of the resulting fragments and routine screening can be used to readily identify expression products having the desired activity.

As used herein, the terms "nucleic acid" and "polynucleotide sequence" refer to a deoxyribonucleotide or ribonucleotide polymer in either single- or double-stranded form, and unless otherwise limited, would encompass known analogs of natural nucleotides that can function in a similar manner as naturally-occurring nucleotides. The polynucleotide sequences include both the DNA strand sequence that is transcribed into RNA and the RNA sequence that is translated into protein. The polynucleotide sequences include both full-length sequences as well as shorter sequences derived from the full-length sequences. It is understood that a particular polynucleotide sequence includes the degenerate codons of the native sequence or sequences which may be introduced to provide codon preference in a specific host cell. Allelic variations of the exemplified sequences also come within the scope of the subject invention. The polynucleotide sequences falling within the scope of the subject invention further include sequences which specifically hybridize with the exemplified sequences under stringent conditions. The nucleic acid includes both the sense and antisense strands as either individual strands or in the duplex. The terms "hybridize" or "hybridizing" refer to the binding of two single-stranded nucleic acids via complementary base pairing.

The phrase "hybridizing specifically to" refers to binding, duplexing, or hybridizing of a molecule to a nucleotide sequence under stringent conditions when that sequence is present in a preparation of total cellular DNA or RNA.

The term "stringent conditions" refers to conditions under which a probe will hybridize to its target sub-sequence, but not to sequences having little or no homology to the target sequence. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a complementary probe. Typically, stringent conditions will be those in which the salt concentration is at least about 0.1 to 1.0N Na ion concentration at a pH of about 7.0 to 7.5 and the temperature is at least about 60° C. for long sequences (e.g., greater than about 50 nucleotides) and at least about 42° C. for shorter sequences (e.g., about 10 to 50 nucleotides).

The terms "isolated" or "substantially pure" when referring to polynucleotide sequences encoding the cell death regulatory proteins or fragments thereof refers to nucleic acids which encode cell death regulatory proteins or peptides and which are no longer in the presence of sequences with which they are associated in nature.

The terms "isolated" or "substantially purified" when referring to the proteins of the subject invention means a chemical composition which is essentially free of other cellular components. It is preferably in a homogenous state and can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. Generally, a substantially purified or isolated protein will comprise more than 80% of all macromolecular species present in the preparation. Preferably, the protein is purified to represent greater than 90% of all macromolecular species present. More preferably, the protein is purified to greater than 95%, and most preferably the protein is purified to essential homogeneity, wherein other macromolecular species are not detected by conventional techniques.

The phrase "specifically binds to an antibody" or "specifically immunoreactive with," when referring to a protein or peptide, refers to a binding reaction which is determinative of the presence of the protein in a heterogeneous population of proteins and other biologics. Thus, under designated immunoassay conditions, the specified antibodies bound to a particular protein do not bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays are routinely used to select antibodies specifically immunoreactive with a protein. See Harlow and Lan (1988) for a description of immunoassay formats and conditions that could be used to determine specific immunoreactivity. The subject invention further concerns antibodies raised against the purified bbc6 molecules or their fragments.

The term "biological sample" as used herein refers to any sample obtained from a living organism or from an organism that has died. Examples of biological samples include body fluids, tissue specimens, and tissue cultures lines taken from patients.

The term "recombinant DNA" or "recombinantly-produced DNA" refers to DNA which has been isolated from its native or endogenous source and modified either chemically or enzymatically to delete naturally-occurring flanking nucleotides or provide flanking nucleotides that do not naturally occur. Flanking nucleotides are those nucleotides which are either upstream or downstream from the described sequence or sub-sequence of nucleotides.

The term "recombinant protein" or "recombinantly-produced protein" refers to a peptide or protein produced using cells that do not have an endogenous copy of DNA able to express the protein. The cells produce the protein because they have been genetically altered by the introduction of an appropriate nucleic acid sequence. The recombinant protein will not be found in association with proteins and other subcellular components normally associated with the cells producing the protein.

It is well known that DNA possesses a fundamental property called base complementarity. In nature, DNA ordinarily exists in the form of pairs of anti-parallel strands, the bases on each strand projecting from that strand toward the opposite strand. The base adenine (A) on one strand will always be opposed to the base thymine (T) on the other strand, and the base guanine (G) will be opposed to the base cytosine (C). The bases are held in apposition by their ability to hydrogen bond in this specific way. Though each individual bond is relatively weak, the net effect of many adjacent hydrogen bonded bases, together with base stacking effects, is a stable joining of the two complementary strands. These bonds can be broken by treatments such as high pH or high temperature, and these conditions result in the dissociation, or "denaturation," of the two strands. If the DNA is then placed in conditions which make hydrogen bonding of the bases thermodynamically favorable, the DNA strands will anneal, or "hybridize," and reform the original double stranded DNA. If carried out under appropriate conditions, this hybridization can be highly specific. That is, only strands with a high degree of base complementarity will be able to form stable double stranded structures. The relationship of the specificity of hybridization to reaction conditions is well known. Thus, hybridization may be used to test whether two pieces of DNA are complementary in their base sequences. It is this hybridization mechanism which facilitates the use of probes of the subject invention to readily detect and characterize DNA sequences of interest.

Polymerase Chain Reaction (PCR) is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki et al., 1985). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA fragment produced in the previous cycle. This results in the exponential accumulation of the specific target fragment, up to several million-fold in a few hours. By using a thermostable DNA polymerase such as Taq polymerase, which is isolated from the thermophilic bacterium *Thermus aquaticus*, the amplification process can be completely automated.

The DNA sequences of the subject invention can be used as primers for PCR amplification. In performing PCR amplification, a certain degree of mismatch can be tolerated between primer and template. Therefore, mutations, deletions, and insertions (especially additions of nucleotides to the 5' end) of the exemplified primers fall within the scope of the subject invention. Mutations, insertions and deletions can be produced in a given primer by methods known to an ordinarily skilled artisan. It is important to note that the mutational, insertional, and deletional variants generated from a given primer sequence may be more or less efficient than the original sequences. Notwithstanding such differences in efficiency, these variants are within the scope of the present invention.

In addition, PCR-amplified DNA may serve as a hybridization probe. In order to analyze DNA using the nucleotide sequences of the subject invention as probes, the DNA can first be obtained in its native, double-stranded form. A number of procedures are currently used to isolate DNA and are well known to those skilled in this art.

One approach for the use of the subject invention as probes entails first identifying by Southern blot analysis of a DNA library all DNA segments homologous with the disclosed nucleotide sequences. Thus, it is possible, without the aid of biological analysis, to know in advance the presence of genes homologous with the polynucleotide sequences described herein. Such a probe analysis provides a rapid diagnostic method.

One hybridization procedure useful according to the subject invention typically includes the initial steps of isolating the DNA sample of interest and purifying it chemically. For example, total fractionated nucleic acid isolated from a biological sample can be used. Cells can be treated using known techniques to liberate their DNA (and/or RNA). The DNA sample can be cut into pieces with an appropriate restriction enzyme. The pieces can be separated by size through electrophoresis in a gel, usually agarose or acrylamide. The pieces of interest can be transferred to an immobilizing membrane in a manner that retains the geometry of the pieces. The membrane can then be dried and prehybridized to equilibrate it for later immersion in a hybridization solution. The manner in which the nucleic acid is affixed to a solid support may vary. This fixing of the DNA for later processing has great value for the use of this technique in field studies, remote from laboratory facilities.

The particular hybridization technique is not essential to the subject invention. As improvements are made in hybridization techniques, they can be readily applied.

As is well known in the art, if the probe molecule and nucleic acid sample hybridize by forming a strong non-covalent bond between the two molecules, it can be reasonably assumed that the probe and sample are essentially identical. The probe's detectable label provides a means for determining in a known manner whether hybridization has occurred.

The nucleotide segments of the subject invention which are used as probes can be synthesized by use of DNA synthesizers using standard procedures. In the use of the nucleotide segments as probes, the particular probe is labeled with any suitable label known to those skilled in the art, including radioactive and non-radioactive labels. Typical radioactive labels include $^{32}P$, $^{35}S$, or the like. A probe labeled with a radioactive isotope can be constructed from a nucleotide sequence complementary to the DNA sample by a conventional nick translation reaction, using a DNase and DNA polymerase. The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting. For synthetic probes, it may be most desirable to use enzymes such as polynucleotide kinase or terminal transferase to end-label the DNA for use as probes.

Non-radioactive labels include, for example, ligands such as biotin or thyroxine, as well as enzymes such as hydrolases or perixodases, or the various chemiluminescers such as luciferin, or fluorescent compounds like fluorescein and its derivatives. The probes may be made inherently fluorescent as described in International Application No. WO93/16094. The probe may also be labeled at both ends with different types of labels for ease of separation, as, for example, by using an isotopic label at the end mentioned above and a biotin label at the other end.

The amount of labeled probe which is present in the hybridization solution will vary widely, depending upon the nature of the label, the amount of the labeled probe which can reasonably bind to the filter, and the stringency of the hybridization. Generally, substantial excesses of the probe will be employed to enhance the rate of binding of the probe to the fixed DNA.

Various degrees of stringency of hybridization can be employed. The more severe the conditions, the greater the complementarity that is required for duplex formation. Severity can be controlled by temperature, probe concentration, probe length, ionic strength, time, and the like. Preferably, hybridization is conducted under stringent conditions by techniques well known in the art, as described, for example, in Keller and Manak, 1987.

Duplex formation and stability depend on substantial complementarity between the two strands of a hybrid, and, as noted above, a certain degree of mismatch can be tolerated. Therefore, the nucleotide sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

The known methods include, but are not limited to:

(1) synthesizing chemically or otherwise an artificial sequence which is a mutation, insertion or deletion of the known sequence;

(2) using a nucleotide sequence of the present invention as a probe to obtain via hybridization a new sequence or a mutation, insertion or deletion of the probe sequence; and (3) mutating, inserting or deleting a test sequence in vitro or in vivo.

It is important to note that the mutational, insertional, and deletional variants generated from a given probe may be more or less efficient than the original probe. Notwithstanding such differences in efficiency, these variants are within the scope of the present invention.

Thus, mutational, insertional, and deletional variants of the disclosed nucleotide sequences can be readily prepared by methods which are well known to those skilled in the art. These variants can be used in the same manner as the instant probe sequences so long as the variants have substantial sequence homology with the probes. As used herein, substantial sequence homology refers to homology which is sufficient to enable the variant to function in the same capacity as the original probe. Preferably, this homology is greater than 50%; more preferably, this homology is greater than 75%; and most preferably, this homology is greater than 90%. The degree of homology needed for the variant to function in its intended capacity will depend upon the intended use of the sequence. It is well within the skill of a person trained in this art to make mutational, insertional, and deletional mutations which are designed to improve the function of the sequence or otherwise provide a methodological advantage.

It is well known in the art that the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid.

The amino acid sequence of the proteins of the subject invention can be encoded by equivalent nucleotide sequences encoding the same amino acid sequence of the protein. Accordingly, the subject invention includes probes which would hybridize with various polynucleotide sequences which would all code for a given protein or variations of a given protein. In addition, it has been shown that proteins of identified structure and function may be constructed by changing the amino acid sequence if such changes do not alter the protein secondary structure (Kaiser and Kezdy, 1984).

A further aspect of the claimed invention are antibodies that are raised by immunization of an animal with a purified protein of the subject invention. Both polyclonal and monoclonal antibodies can be produced using standard procedures well known to those skilled in the art using the proteins of the subject invention as an immunogen (see, for example, *Monoclonal Antibodies: Principles and Practice*, 1983; *Monoclonal Hybridoma Antibodies: Techniques and Applications*, 1982; *Selected Methods in Cellular Immunology*, 1980; *Immunological Methods, Vol. II*, 1981; *Practical Immunology*, and Kohler et al., 1975).

The proteins of the subject invention include those which are specifically exemplified herein as well as related proteins which, for example, are immunoreactive with antibodies which are produced by, or are immunologically reactive with, the proteins specifically exemplified herein.

The proteins described herein can be used in therapeutic or diagnostic procedures. These proteins can also be used as molecular weight standards in protein analysis procedures.

Following are examples which illustrate procedures for practicing the invention. These examples should not be construed as limiting. All percentages are by weight and all solvent mixture proportions are by volume unless otherwise noted.

EXAMPLE 1

Specificity of Integration Between bbc6 and Bcl-2

The Matchmaker yeast two-hybrid system (available from Clontech Laboratories, Palo Alto, Calif.) was used to evaluate the interaction between bbc6 and Bcl-2. This experiment was done in yeast two-hybrid reporter strain Y190. Y190 was transformed with 12 different combinations of DNA clones, listed below. After the colonies of transformants had grown up in the selection medium plate, individual colonies were patched onto a single selection plate (SD-leu/-Try) and allowed to grow for 2 additional days at 30° C. All 12 slots of the plate had about an equal amount of yeast cells grown to saturation within 2 days. Then a lift assay was performed according to the standard protocol. A blue color in patched yeast colony represents a positive signal which indicates an interaction between the two DNA clone inserts. A white color represents a negative signal which indicates no interaction. The results are shown in Table 1.

TABLE 1

| Number | Combination | Interacton result |
|---|---|---|
| 1 | bbc6 with pGBT9 | negative |
| 2 | bbc6 with Bcl-2 | positive |
| 3 | bbc6 with pLAM5' | negative |
| 4 | p53 + clone-1 with pGBT9 | negative |
| 5 | p53 + clone-1 with pVA3 | positive |
| 6 | p53 + clone-1 with pLAM5' | negative |
| 7 | pTD1 with pGBT9 | negative |
| 8 | pTD1 with pVA3 | positive |
| 9 | pTD1 with pLAM5' | negative |
| 10 | p53 + clone-2 with pGBT9 | positive |
| 11 | p53 + clone-2 with pVA3 | positive |
| 12 | p53 + clone-2 with pLAM5' | positive |

If a clone (e.g., p53+clone-1) interacts specifically with its bait (pVA3 in this case), then only the yeast co-transformed with the bait and itself (#5 in Table 1) will show the positive signal (blue). Yeasts co-transformed with the empty vector (pGBT9) or unrelated bait (pLAM5') should not show any positive signals (#4 and #6).

If a clone (e.g., p53+clone-2) does not interact with its bait specifically, then yeasts co-transformed with the clone (p53+clone-1) and either the bait (pVA3), or the empty vector (pGBT9), or unrelated bait (pLAM5') will show positive signals.

In a positive control experiment, pTD1 (which encodes SV40 T antigen) was introduced into yeast reporter strain by co-transformation with the empty vector (#7, pGBT9), or its specific bait p53 (#8, pVA3), or an unrelated bait (#9, pLAM5'). Only in the case of its specific bait p53 (#8, pVA3) was a positive signal observed.

EXAMPLE 2

Expression of BBC6

BBC6 mRNA is approximately 1.2 kb. It is preferentially expressed in heart, brain, placenta, prostate, testis, ovary, small intestine, lymphoblastic leukemia cell line MOLT-4, Burkitt's lymphoma cell line Raji, and colorectal adenocarcinoma cell line SW480. BBC6 expression is low in spleen, thymus, or normal leukocytes, but high in certain leukemia cell lines.

In accordance with the subject invention, leukocytes can be assayed for evidence of BBC6 expression. Such expression can be determined by detecting the protein itself or the presence of BBC6 mRNA. The protein can readily be detected, for example, using antibodies to BBC6 produced as described herein.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

U.S. Patents
U.S. Pat. No. 4,683,195.
U.S. Pat. No. 4,683,202.
U.S. Pat. No. 4,800,159.

Foreign Patent Documents
WO93/16094.

Other References

Boise, L. H., M. González-Garcia, C. E. Posteme, L. Ding, T. Lindsten, L. A. Turka, X. Mao, G. Nuñez, C. B. Thompson (1993) "bcl-x, a bcl-2-related gene that functions as a dominant regulator of apopototic cell death," *Cell* 74:597–608.

Garcia, I., I. Martinou, Y. Tsujimoto, J. -C. Martinou (1992) "Prevention of programmed cell death of sympathetic neurons by the bcl-2 proto-oncogene," *Science* 258:302–304.

Goding, J. W., ed. (1983) *Monoclonal Antibodies: Principles and Practice*, Academic Press, London.

Harlow and Lan (1988) *Antibodies, A Laboratory Manual*, Cold Spring Harbor Publications, New York.

Hengartner, M. O., H. R. Horvitz (1994) "*C. elegans* cell survival gene ced-9 encodes a functional homolog of the mammalian proto-oncogene bcl-2," *Cell* 76:665–676.

Hudson, L., F. C. Hay (1980) *Practical Immunology*, Blackwell Scientific Publications, Oxford, pp. 303–326.

Hurrell, J. G. R., ed. (1982) *Monoclonal Hybridoma Antibodies: Techniques and Applications*, CRC Press, Boca Raton.

Kaiser, E. T., Kezdy, F. J. [1984]*Science* 223:249–255.

Keller, G. H., M. M. Manak (1987) *DNA Probes*, Stockton Press, New York, N.Y., pp. 169–170.

Kozopas, K. M., T. Yang, H. L. Buchan, P. Zhou, R. W. Craig (1993) "MCL-1, a gene expressed in programmed myeloid cell differentiation, has sequence similarity to BCL-2," *Proc. Natl. Acad. Sci. USA* 90:3516–3520.

Kohler, G., C. Milstein (1975) *Nature* 256:495–497.

Lefkovits, I., B. Pernis, eds. (1981) *Immunological Methods, Volume II*, Academic Press, London.

Lin, E. Y., A. Orlofsky, M. S. Berger, M. B. Prystowsky (1993) "Characterization of A1, a novel hemopoietic-specific early-response gene with sequence similarity to bcl-2," *J. Immunol.* 151:1879–1988.

Lefkovits, I., B. Pernis, eds. (1981) *Immunological Methods, Volume II*, Academic Press, London.

Mishell, B. B., S. M. Shiigi, eds. (1980) *Selected Methods in Cellular Immunology*, W. H. Freeman and Company, San Francisco.

Oltvai, Z. N., C. L. Millliman, S. J. Korsmeyer (1993) "Bcl-2 heterodimerizes in vivo with a conserved homolog, Bax, that accelerates programmed cell death," *Cell* 74:609–619.

Saiki, Randall K., Stephen Schaff, Fred Faloona, Kary B. Mullis, Glenn T. Horn, Henry A. Erllch, Norman Arnheim (1985) "Enzymatic Amplification of β-Globin Genomic Sequences and Restriction Site Analysis for Diagnosis of Sickle Cell Anemia," *Science* 230:1350–1354.

Strasser, A., A. W. Harris, S. Cory (1991) "bcl-2 transgene inhibits T cell death and perturbs thymic serf-censorship," *Cell* 67:889–899.

Vaux, D. L., S. Cory, J. M. Adams (1988) "Bcl-2 gene promotes haemopoietic cell survival and cooperates with c-myc to immortalize pre-B cells," *Nature* 335:440–442.

Vaux, D. L., I. L. Weissman, S. K. Kim (1993) "Molecular regulation of apoptosis: genetic controls on cell death," *Cell* 74:777–779.

Williams, G. T., C. A. Smith (1993) "Molecular regulation of apoptosis: genetic controls on cell death," *Cell* 74:777–779.

Yin, X. -M., Z. N. Oltval, S. J. Korsmeyer (1994) "BH1 and BH2 domains of Bcl-2 are required for inhibition of apoptosis and heterodimerization with Bax," *Nature* 369:321–323.

I claim:

1. An isolated polynucleotide which encodes the amino acid sequence shown in SEQ ID NO. 2, or a biologically active allelic variation thereof.

2. An isolated polynucleotide which consists of the nucleotide sequence shown in SEQ ID NO. 1, or a biologically active allelic variation thereof.

* * * * *

UNITED STATES PATENT AND TRADEMARK OFFICE
CERTIFICATE OF CORRECTION

PATENT NO.   : 5,663,316
DATED        : September 2, 1997
INVENTOR(S)  : Yin Xudong It is certified that error appears in the above-identified patent and that said Letters Patent is hereby corrected as shown below:

Column 1, lines 27&28: "(Olwai et al., 1993;" should read --(Oltvai *et al.*, 1993;--

Column 10, line 17: "Stephen Schaff," should read --Stephen Scharf,-- line 18: "Henry A. Erllch," should read --Henry A. Erlich,-- lines 24&25: "serf-censorship," should read --self-censorship,--

Signed and Sealed this

Ninth Day of December, 1997

*Attest:*

*Attesting Officer*

BRUCE LEHMAN

Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 944 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
CGTGGTCGAC  GGCCCGGGCT  GGTCTGTGCC  TTGACTACGT  AACATCTTGT  CCTCACAGCC      60

CAGAGCATGT  TCCAGATCCC  AGAGTTTGAG  CCGAGTGAGC  AGGAAGACTC  CAGCTCTGCA     120

GAGAGGGCT  GGCGCAGCCC  CGCAGGGACG  GGCCCTCAGG  CTCCGGCAAG  CATCATCGCC     180
```

| | | | | | |
|---|---|---|---|---|---|
| AGGCCCCAGG | TCCTGTGGGA | CGCCAGTCAC | CAGCAGGAGC | AGCCAACCAG | CAGCAGCCAT | 240 |
| CATGGAGGCG | CTGGGGCTGT | GGAGATCCGG | AGTCGCCACA | GCTCCTACCC | CGCGGGGACG | 300 |
| GAGGACGACG | AAGGGATGGG | GGAGGAGCCC | AGCCCCTTTC | GGGGCGCTCG | CGCTCGGCCG | 360 |
| CCCCCCAACC | TCTGGGCAGC | ACAGCGCTAT | GGCCGCGAGC | TCCGGAGGAT | GAGTGACGAG | 420 |
| TTTGTGGACT | CCTTTAAGAA | GGGACTTCCT | CGCCCGAAGA | GCGCGGGCAC | AGCAACGCAG | 480 |
| ATGCGGCAAA | GCTCCAGCTG | GACGCGAGTC | TTCCAGTCCT | GGTGGGATCG | GAACTTGGGC | 540 |
| AGGGGAACTG | CCGCCCCCTC | CCAGTGACCT | TCGCTCCACA | TCCCGAAACT | CCACCCGTTC | 600 |
| CCACTGCCCT | GGGCAGCCAT | CTTGAATATG | GGCGGAAGTA | CTTCCCTCAG | GCCTATGCAA | 660 |
| AAAGAGGATC | CGTGCTGTCT | CCTTTGGAGG | GAGGGCTGAC | CCAGATTCCC | TTCCGGTGCG | 720 |
| TGTGAAGCCA | CGGAAGGCTT | GGTCCCATCG | GAAGTTTTGG | GTTTTCCGCC | CACAGCCGCC | 780 |
| GGAAGTGGCT | CCGTGGCCCC | GCCCTCAGGT | CCGGGCTTTC | CCCAGGCGC | CTGCGTAAGT | 840 |
| CGCGAGCCAG | GTTTAACCGT | TGCGTCACCG | GGACCCGAGC | CCCCGCGATG | CCCTGGGGCG | 900 |
| CGTGCTCACT | ACCAAATGTT | AATAAAGCCC | GCGTCTGTGC | CGCC | | 944 |

( 2 ) INFORMATION FOR SEQ ID NO:2:

( i ) SEQUENCE CHARACTERISTICS:
        ( A ) LENGTH: 166 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Met Phe Gln Ile Pro Glu Phe Glu Pro Ser Glu Gln Glu Asp Ser Ser
  1               5                  10                  15

Ser Ala Glu Arg Gly Trp Arg Ser Pro Ala Gly Thr Gly Pro Gln Ala
             20                  25                  30

Pro Ala Ser Ile Ile Ala Arg Pro Gln Val Leu Trp Asp Ala Ser His
             35                  40                  45

Gln Gln Glu Gln Pro Thr Ser Ser Ser His His Gly Gly Ala Gly Ala
         50                  55                  60

Val Glu Ile Arg Ser Arg His Ser Ser Tyr Pro Ala Gly Thr Glu Asp
 65                  70                  75                  80

Asp Glu Gly Met Gly Glu Glu Pro Ser Pro Phe Arg Gly Ala Arg Ala
                 85                  90                  95

Arg Pro Pro Pro Asn Leu Trp Ala Ala Gln Arg Tyr Gly Arg Glu Leu
                100                 105                 110

Arg Arg Met Ser Asp Glu Phe Val Asp Ser Phe Lys Lys Gly Leu Pro
            115                 120                 125

Arg Pro Lys Ser Ala Gly Thr Ala Thr Gln Met Arg Gln Ser Ser Ser
        130                 135                 140

Trp Thr Arg Val Phe Gln Ser Trp Trp Asp Arg Asn Leu Gly Arg Gly
145                 150                 155                 160

Thr Ala Ala Pro Ser Gln
                165
```